United States Patent [19]

Mori

[11] Patent Number: 4,844,069
[45] Date of Patent: Jul. 4, 1989

[54] LIGHT RAYS RADIATION DEVICE FOR MEDICAL TREATMENT

[76] Inventor: Kei Mori, 3-16-3-501, Kaminoge, Setagaya-ku, Tokyo, Japan

[21] Appl. No.: 157,089

[22] Filed: Feb. 9, 1988

Related U.S. Application Data

[63] Continuation of Ser. No. 882,663, Jul. 7, 1986, abandoned.

[30] Foreign Application Priority Data

Jul. 10, 1985 [JP] Japan ............................ 60-105237[U]
Jul. 10, 1985 [JP] Japan ............................ 60-105238[U]
Jul. 17, 1985 [JP] Japan ............................ 60-109186[U]

[51] Int. Cl.$^4$ .............................................. A61N 5/06
[52] U.S. Cl. .................................... 128/396; 128/395; 362/147; 362/407
[58] Field of Search ............... 128/395, 396, 397, 398; 362/32, 407, 804, 147

[56] References Cited

U.S. PATENT DOCUMENTS

| | | | |
|---|---|---|---|
| 1,421,756 | 7/1922 | Amao | 128/396 |
| 2,212,975 | 8/1940 | Boynton | 128/396 |
| 2,858,381 | 10/1958 | Goldberg et al. | 362/407 |
| 3,642,007 | 2/1972 | Roberts et al. | 128/395 |
| 3,818,914 | 6/1974 | Bender | 128/396 |
| 4,011,403 | 3/1977 | Epstein et al. | 362/32 |
| 4,152,752 | 5/1979 | Niemi | 362/147 |
| 4,459,986 | 7/1984 | Karaki | 128/395 |
| 4,503,854 | 3/1985 | Jako | 128/395 |
| 4,616,304 | 10/1986 | Von Kohorn | 362/806 |

FOREIGN PATENT DOCUMENTS

| | | | |
|---|---|---|---|
| 2922357 | 12/1980 | Fed. Rep. of Germany | 128/396 |
| 2936471 | 3/1981 | Fed. Rep. of Germany | 128/395 |
| 1121119 | 7/1956 | France | 128/395 |
| 788475 | 9/1981 | U.S.S.R. | 128/398 |

Primary Examiner—Michael Safavi
Attorney, Agent, or Firm—Jordan and Hamburg

[57] ABSTRACT

A light rays radiation device for medical treatment, or providing beauty treatment or health promotion etc. comprises an optical conductor for transmitting therethrough light rays corresponding to the visible light rays component of solar rays, a lens for focusing the light rays emitted from the optical conductor, the lens being mounted so as to oppose the light rays emitting end of the optical conductor, a holder member for unitarily holding the light rays emitting end of the optical conductor and the lens, and a vertically-suspended guide bar capable of moving the lens and the light-rays emitting end of the optical conductor in a vertical axial direction and fixing both of them at an optional position.

10 Claims, 3 Drawing Sheets

LIGHT RAYS RADIATION DEVICE FOR MEDICAL TREATMENT

This application is a continuation of application Ser. No. 882,663, filed July 7, 1986 now abandoned.

BACKGROUND OF THE INVENTION

The present invention relates to a light rays radiation device for medical or beauty treatment, in particular, a light rays radiation device for performing various medical treatments or providing beauty treatment or health promotion etc. by radiating light energy corresponding to the visible light rays component of solar rays onto the diseased part of a patient or providing beauty treatment or health promotion, etc. by radiating the same onto the surface of a patient's skin.

In the recent years, a large number of persons suffer from incurable diseases such as arthritis, neuralgia and rheumatism, or suffer pain from an injury or a bone fracture, or pain of an ill-defined disease. Furthermore, a person cannot avoid one's skin from aging which progresses gradually from comparatively young ages. On the other hand, the present applicant has previously proposed to focus solar rays or artificial light rays by use of lenses or the like, to guide the same into an optical conductor, and to transmit these rays onto an optional desired place through the optical conductor. These solar rays or artificial light rays transmitted in such a way are employed for use in illuminating or for other like purposes, for example, to cultivate plants, chlorella, or the like. On the process thereof, visible light rays not containing ultraviolet, infrared, etc. promote a reaction in a living body, and thereby promotes health of a person or prevents aging of the person's skin. Furthermore, those visible light rays have noticeable effects of stopping the pain of arthritis, neuralgia, bedsore, rheumatism, injuries, bone fractures, or the like. Such effects obtained by use of the device according to the present invention have been already found by the present applicant.

SUMMARY OF THE INVENTION

It is an object of the present invention to provide a light rays radiation device capable of radiating light rays corresponding to the visible light rays component of solar rays which contain no harmful component such as ultraviolet or infrared, etc.

It is another object of the present invention to provide a light rays radiation device for medical treatment capable of performing various medical treatment or providing beauty treatment or health promotion, etc.

The above-mentioned features and other advantages of the present invention will be apparent from the following detailed description which goes with the accompanying drawings.

DESCRIPTION OF THE PREFERRED EMBODIMENTS

The present invention relates to a light rays radiation device for medical treatment, in particular, a light rays radiation device for performing various medical treatments or providing beauty treatment or health promotion etc. by radiating light energy corresponding to the visible light rays component of solar rays onto the diseased part of a patient or providing beauty treatment or health promotion, etc. by radiating the same onto the surface of a patient's skin.

Figure 1:
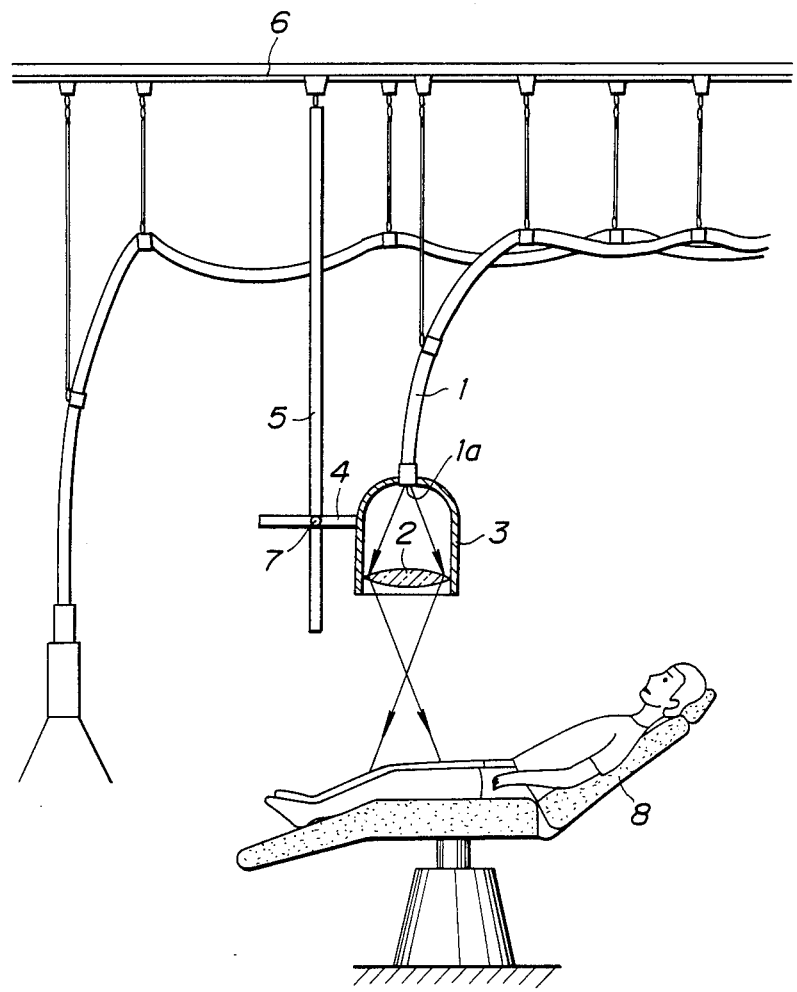
FIG. 1 is an elevational view for explaining one embodiment of a light rays radiation device for medical treatment according to the present invention.

In FIG. 1, 1 is an optical conductor cable. Solar rays or artificial light rays are guided into the optical conductor cable 1 from an end portion thereof not shown in FIG. 1, and the guided light rays are transmitted therethrough. Light rays (white light rays) corresponding to the visible light rays component of solar rays are transmitted through the optical conductor cable 1 in such a manner as proposed previously by the present applicant in various ways. A lens 2 is mounted so as to oppose the light rays emitting end 1a of the above-mentioned optical conductor cable 1. A holder member 3 is provided for holding the lens 2 and the light rays emitting end 1a of the optical conductor cable 1, the lens 2 being held in the holder member 3 at a predetermined distance from the light rays emitting end 1a of the optical conductor cable 1. An operation arm 4 extends from the holder member 3, and a vertically-suspended guide bar 5 guides the operation arm 4 so as to move the same up and down. A suspension rail 6 is capable of moving the guide bar 5, 7 and a bolt for fixing the operation arm 4 to the guide bar 5. A chair 8 is provided for medical treatment.

A patient lies on the chair for medical treatment 8. In order to move the holder member 3 up and down, and right and left, the operation arm 4 is gripped. By moving the holder member 3, the light rays transmitted through the optical conductor cable 1 are applied to the diseased part of the patient so as to form an image of a desired size. Next, the holder member 3 is fixed at a desired position by use of the bolt 7. From this time, the light rays are applied to the diseased part during a desired period of time.

As mentioned heretofore, only the visible light rays component of the solar rays or the artificial light rays is applied to the diseased part, according to the present invention. Consequently there is no harmful influence exerted by ultraviolet or infrared rays at all. Especially, in the case of ultraviolet rays contained in the light rays, cancer grows in the human body as a result of ultraviolet accumulation. On the other hand, in the case of infrared rays contained in the light rays, the temperature rises too much, and thereby a desired amount of light radiation cannot be effected as a result of the infrared accumulation.

According to the present embodiment, the problem of such harmful influence has been settled completely. For instance, even though the amount of light radiation increases considerably, the light rays can be applied to the diseased part of the patient without suffering from any harmful influence. Therefore, it may be possible to cure diseased parts in a short period of time.

Figure 2:
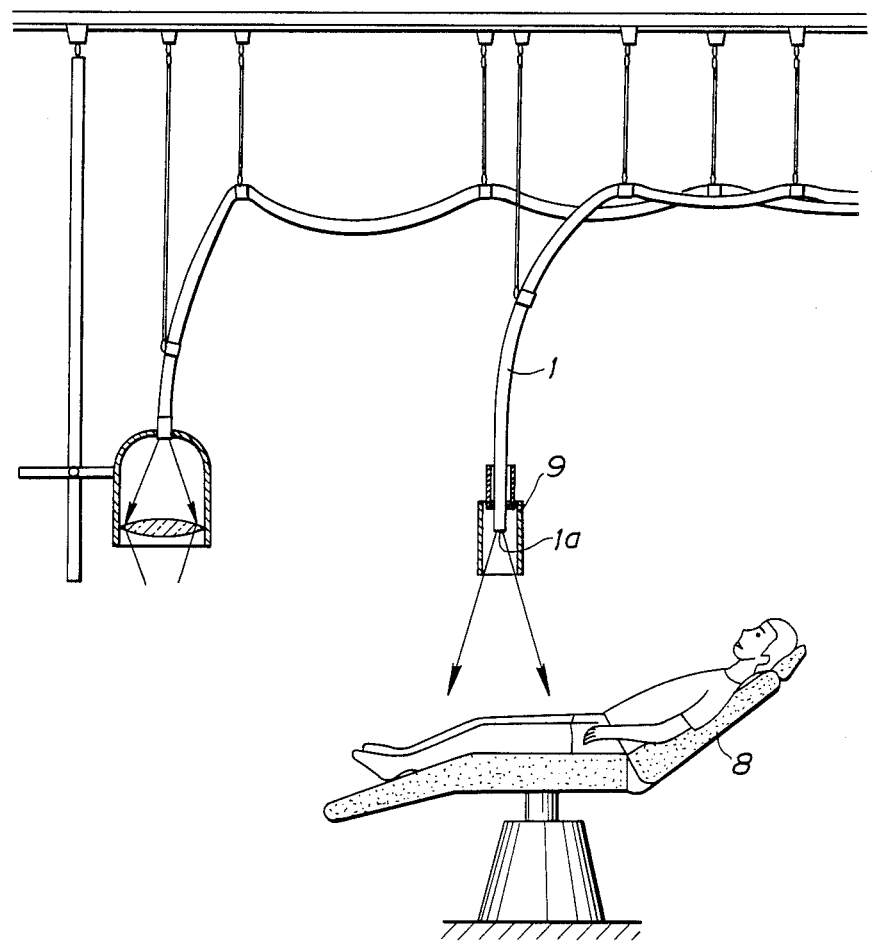
FIG. 2 is an elevational view for explaining another embodiment of a light rays radiation device for medical treatment according to the present invention.

In FIG. 2, 1 is an optical conductor cable. Solar rays or artificial light rays are guided into the optical conductor cable 1 from an end portion thereof not shown in FIG. 1, and the guided light rays are transmitted therethrough. Light rays (white light rays) corresponding to the visible light rays component of solar rays are transmitted through the optical conductor cable 1 in such a manner as proposed previously by the present applicant in various ways. A semi-transparent cylindrical hood member 9 is installed at a light rays emitting end portion 1a of the optical conductor cable 1, and a chair 8 for medical treatment is provided. At the time of medical treatment, a patient lies on the chair 8 for medical treatment. The light rays comprising the visible light rays component transmitted through the optical conductor cable 1 in such a manner as mentioned heretofore are applied to the diseased part of the patient.

As mentioned above, the light rays to be applied to the diseased part of the patient correspond to the visible light rays component of the solar rays and contain therein neither ultraviolet nor infrared. Thereby, it may be possible to perform medical treatment without suffering from any harmful influence exerted by ultraviolet or infrared rays.

However, in the case of utilizing the solar rays in practice, the visible light rays component of the solar rays varies every hour. Therefore, the positional relationship between the focus of the lens for focusing the solar rays and the light rays receiving end of the optical conductor cable for guiding therein the solar rays focused by the lens changes. As a result, the light rays component guided into the optical conductor cable 1 also changes, but it is difficult to recognize the change of the light rays component with the naked eye.

On the other hand, the present applicant has already found that, when the light rays comprising of the visible light rays component transmitted through the optical conductor cable in such a manner as mentioned above pass through a translucent member, the translucent member becomes colored.

The present embodiment has been made on the basis of this discovery. As shown in FIG. 2, a translucent hood 9 is installed at the light rays emitting end portion 1a of the optical conductor 1. When there are too many red component light rays contained in the visible light rays component, the hood becomes red-colored. When there are too many green component light rays contained in the visible light rays component, the hood becomes green-colored. Thereby, the condition of the light component applied to the diseased part of the patient can be known in broad outline.

As mentioned heretofore, only the visible light rays component of the solar rays or the artificial light rays is applied to the diseased part, according to the present invention. Consequently, there is no harmful influence exerted by the ultraviolet or infrared rays at all. Especially, in the case of the ultraviolet contained in the light rays, cancer grows in the human body as a result of ultraviolet accumulation. On the other hand, in the case of infrared contained in the light rays, the temperature rises too much, and thereby a desired amount of light radiation cannot be performed as a result of infrared accumulation.

According to the present embodiment, the problem of such harmful influence has been settled completely. For instance, even though the amount of light radiation increases considerably, the light rays can be applied to the diseased part of the patient without suffering from any harmful influence. Therefore, it may be possible to cure diseased parts in a short period of time.

Figure 3:
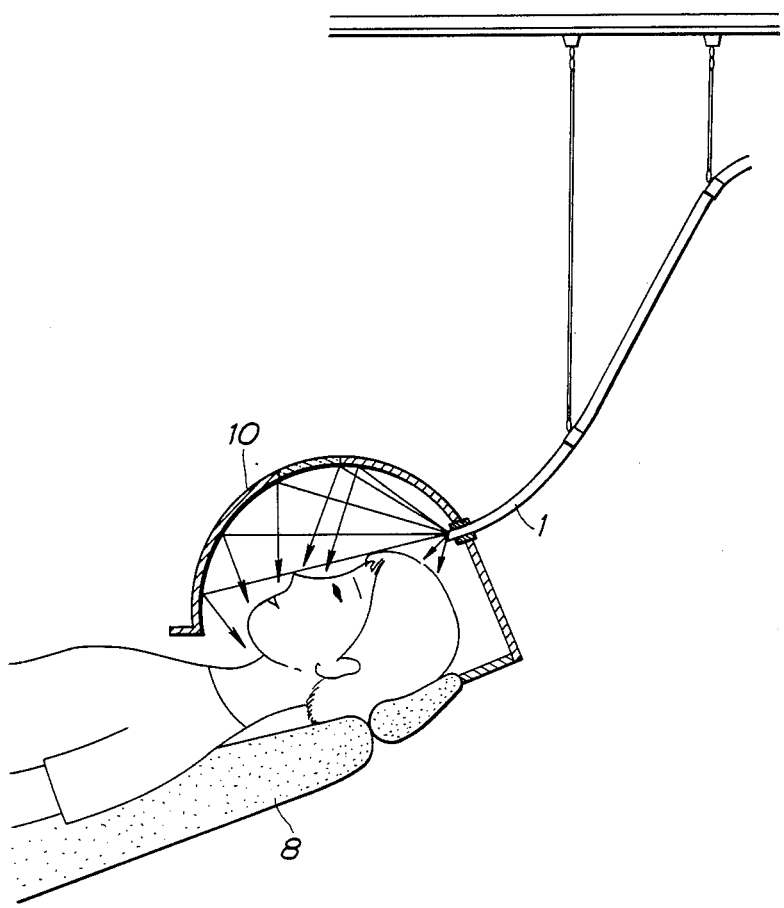
FIG. 3 is an elevational view for explaining another embodiment of a light rays radiation device for beauty treatment or health promotion according to the present invention.

In FIG. 3, 1 is an optical conductor cable. Solar rays or artificial light rays are guided into the optical conductor cable 1 from an end portion thereof not shown in FIG. 1, and the guided light rays are transmitted therethrough. Light rays (white light rays) corresponding to the visible light rays component of solar rays are transmitted throgh the optical conductor cable 1 in such a manner as proposed previously by the present applicant in various ways.

The numeral 10 represents a reflection hood for covering the face of a person. The inner surface of the reflection hood 10 has a reflection surface. The reflection hood is so constructed that the optical conductor cable 1 can be mounted on and removed from the reflection hood 10. The light rays transmitted through the optical conductor cable 1 as mentioned above are emitted into the reflection hood, and reflected therein and applied to the face of a person. Moreover, it may be also possible to construct the reflection hood so as to apply the light rays not only to the face, but to the head. Furthermore, the reflection hood is employed so as to cover the face and the area neighboring the eyes is formed with transparent material so that a person covered with the hood can see outside of the hood. The reflection hood 10 is equipped so as to be mounted on and removed from the chair 8. Alternatively, the hood may be suspended from the ceiling. In such a manner as mentioned above, load of the reflection hood 10 is imparted to the head of a person as slightly as possible.

As mentioned heretofore, according to the present invention, the light rays to be applied to the face or the head of a person correspond to the visible light rays component of the solar rays which contains neither ultraviolet nor infrared. Thereby, beauty treatment or health promotion can be provided without suffering from any harmful influence exerted by ultraviolet or infrared, etc. Especially, in the case of ultraviolet contained in the light rays, cancer grows in the human body as a result of ultraviolet accumulation. On the other hand, in the case of infrared contained in the light rays, the temperature rises too much, and thereby a desired amount of light radiation cannot be performed as a result of infrared accumulation.

According to the present invention, the problem of such harmful influence has been settled completely. As a result, a desired amount of the light rays can be radiated during a desired period of time.

I claim:

1. A medical treatment device utilizing the visible light ray component of solar rays, comprising an optical conductor receiving and transmitting therethrough light rays corresponding to the visible light rays component of solar rays and excluding ultraviolet and infrared rays, said conductor having a light emitting end portion, a holder means on which said light emitting end portion is mounted, a lens means mounted on said holder means in a position spaced from said light emitting end portion for focusing light rays emitted from said light emitting end portion, and guide means for movably mounting said holder means such that an operator can move the holder means along with said light emitting end portion and said lens to a desired position to direct the visible light rays focused by said lens to a desired position on a patient's body to thereby effect medical treatment thereof.

2. A medical treatment device according to claim 1, wherein said holder means comprises a hood having a generally cylindrical body portion having two ends, one of said ends being open and the other of said ends having a generally partial spherical configuration, said lens means being mounted at said open end of said hood, said light emitting end portion being mounted on said other end of said hood such that the light rays emitted from said light emitting end portion of said conductor pass through the interior of said hood to said lens means.

3. A medical treatment device utilizing the visible light ray component of solar rays comprising an optical conductor receiving and transmitting therethrough light rays corresponding to the visible light rays component of solar rays and excluding ultraviolet and infrared rays, said conductor having a light emitting end portion, a holder means on which said light emitting end portion is mounted, and guide means for movably mounting said holder means such that an operator can move the holder means along with said light emitting end portion to a desired position to direct the visible light rays emitted from said light receiving end of said conductor to a desired position on a patient's body to thereby effect medical treatment thereof.

4. A medical treatment device according to claim 3, wherein said holder means comprises a hood having a generally cylindrical configuration with two ends, one of said ends being open and the other of said ends receiving said light emitting end portion of said optical conductor.

5. A medical treatment device according to claim 4, wherein said hood is made of a translucent material which changes color corresponding to the color of the light rays color component transmitted to said hood by said conductor.

6. A medical treatment device according to claim 3, wherein said holder means comprises a hood having an arcuate portion to be disposed adjacent to a part of a person's body, and reflector means on the inner surface of said arcuate portion for reflecting said light rays received from said light emitting end portion of said conductor onto said adjacent part of the person's body.

7. A medical treatment device according to claim 6, wherein said arcuate portion has a partial spherical configuration.

8. A medical treatment device according to claim 7, wherein said hood comprises an enclosure structure which receives a patient's head, said spherical portion overlying said patient's face.

9. A medical treatment device according to claim 8 further comprising a chair for receiving said patient, said enclosure structure being mounted on said chair such that the patient's head is disposed in said enclosure structure while reclining on said chair.

10. A medical treatment device according to claim 9, wherein at least parts of said enclosure structure are made of a transparent material to permit the patient to see outside of said enclosure structure.

* * * * *